(12) United States Patent
Jeanne et al.

(10) Patent No.: US 10,631,965 B2
(45) Date of Patent: Apr. 28, 2020

(54) METHOD AND APPARATUS FOR PROTECTION OF SOFT TISSUES AGAINST A TEETH WHITENING SUBSTANCE

(71) Applicant: KONINKLIJKE PHILIPS N.V., Eindhoven (NL)

(72) Inventors: Vincent Jeanne, Migne Auxances (FR); Meng Peng, Bothell, WA (US); Jianxun Feng, Bothell, WA (US); Wan-Tzu Chen, Lake Forest Park, WA (US); Evan Dak Wah Dengler, Seattle, WA (US); Sungsoo Lee, Kirkland, WA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 0 days.

(21) Appl. No.: 16/086,453

(22) PCT Filed: Dec. 4, 2017

(86) PCT No.: PCT/EP2017/081282
§ 371 (c)(1),
(2) Date: Sep. 19, 2018

(87) PCT Pub. No.: WO2018/104190
PCT Pub. Date: Jun. 14, 2018

(65) Prior Publication Data
US 2019/0290413 A1    Sep. 26, 2019

Related U.S. Application Data

(60) Provisional application No. 62/430,958, filed on Dec. 7, 2016.

(51) Int. Cl.
| A61C 19/06 | (2006.01) |
| A61B 1/24  | (2006.01) |
| A61B 5/00  | (2006.01) |

(52) U.S. Cl.
CPC .............. *A61C 19/066* (2013.01); *A61B 1/24* (2013.01); *A61B 5/0088* (2013.01); *A61B 5/742* (2013.01); *A61B 5/7405* (2013.01); *A61B 5/7455* (2013.01)

(58) Field of Classification Search
CPC ..... A61C 19/04; A61C 19/063; A61C 19/066; G01J 3/508; A61B 5/4547; A61B 1/24;
(Continued)

(56) References Cited

U.S. PATENT DOCUMENTS

| 9,757,065 B1* | 9/2017 | Suri ..................... A61B 5/4833 |
| 2002/0127143 A1* | 9/2002 | Kuo ................... A61B 10/0051 |
| | | 422/68.1 |

(Continued)

FOREIGN PATENT DOCUMENTS

| WO | 20040847852 A2 | 10/2004 |
| WO | 2006098719 A1 | 9/2006 |

(Continued)

*Primary Examiner* — Sean M Michalski
*Assistant Examiner* — Shannel N Wright (57) ABSTRACT

A whitening smart pen apparatus (10) for automatically dispensing a teeth whitening substance onto one or more teeth of a user comprises a fluid reservoir (16), a nozzle (18) having an output port (26), a fluid dispenser (20), a sensor (22) and a controller (24). The fluid dispenser dispenses the teeth whitening substance from the fluid reservoir to the nozzle and is output via the output port. The sensor, positioned in an advance dispensing direction of the nozzle, senses a target surface that comprises either (i) a tooth surface (12) or (ii) other surface (14). The controller (24) is configured for (i) controlling a gating of the fluid dispenser (20) to dispense the teeth whitening substance from the fluid reservoir (16) in response to the sensor (22) detecting the tooth surface (12), and (ii) stopping or disabling the gating of the fluid dispenser to stop or disable a dispensing of the
(Continued)

teeth whitening substance from the fluid reservoir in response to the sensor (22) detecting the other surface (14).

13 Claims, 4 Drawing Sheets

(58) Field of Classification Search
CPC ..... A61B 5/0088; A61B 5/7405; A61B 5/742; A61B 5/7455; A61B 5/746
See application file for complete search history.

(56) References Cited

U.S. PATENT DOCUMENTS

| | | |
|---|---|---|
| 2005/0249677 A1 | 11/2005 | Malcmacher et al. |
| 2007/0111167 A1* | 5/2007 | Russell ............... A46B 15/0002 433/216 |
| 2008/0060148 A1* | 3/2008 | Pinyayev ............. A61B 5/0088 15/22.1 |
| 2009/0060622 A1* | 3/2009 | Lian ................... A46B 11/0006 401/28 |
| 2012/0160263 A1* | 6/2012 | Kotlarchik ......... A61C 17/0202 132/322 |
| 2012/0251971 A1* | 10/2012 | Fish ................... A46B 15/0002 433/27 |
| 2013/0296811 A1 | 11/2013 | Bangera et al. |
| 2015/0044628 A1* | 2/2015 | Flyash ................ A61C 19/066 433/27 |
| 2015/0282912 A1* | 10/2015 | Prins .................. A46B 15/0002 433/80 |
| 2015/0305626 A1* | 10/2015 | Deane ................. A61B 5/7228 433/27 |
| 2016/0262531 A1 | 9/2016 | Hellkamp |
| 2016/0338635 A1* | 11/2016 | Johnson ............... A61B 5/4547 |
| 2016/0338810 A1* | 11/2016 | Schmalhurst ........ A46B 11/002 |
| 2017/0000352 A1* | 1/2017 | Deane ................. A61B 5/0071 |
| 2017/0231735 A1* | 8/2017 | Young ............... A61B 1/00006 433/29 |
| 2019/0080451 A1* | 3/2019 | Iglehart .................. G01J 3/027 |

FOREIGN PATENT DOCUMENTS

| | | |
|---|---|---|
| WO | 2007073917 A1 | 7/2007 |
| WO | 2009042085 A1 | 4/2009 |
| WO | 2011077299 A1 | 6/2011 |
| WO | 20150978580 A1 | 7/2015 |

* cited by examiner

METHOD AND APPARATUS FOR PROTECTION OF SOFT TISSUES AGAINST A TEETH WHITENING SUBSTANCE

CROSS-REFERENCE TO PRIOR APPLICATIONS

This application is the U.S. National Phase application under 35 U.S.C. § 371 of International Application No. PCT/EP2017/081282, filed on Dec. 4, 2017, which claims the benefit of U.S. Provisional Patent Application No. 62/430,958, filed on Dec. 7, 2016. These applications are hereby incorporated by reference herein.

The present embodiments relate generally to handheld appliances for whitening teeth, and particularly, to a whitening smart pen apparatus and method which provides protection for the soft tissues during the teeth whitening process.

Whether patients want a confidence boost or just to look their best, whitening remains the most-requested cosmetic dental procedure. As such procedure is complex and involves usage of chemical component (hydrogen peroxide) it is originally designed to take place in dental offices and operated by professional. Due to growing consumer interest for such treatment, take-home whitening solutions are becoming available on the market.

Since teeth whitening requires the use of chemical components which are not designed to be in contact with human tissue, safety is of extreme relevance. This safety aspect is ensured by professionals when performed in dental offices; however commercially available retail whitening solutions rely solely on users to apply chemicals to cover the entire tooth surface while avoiding contamination on gum and other soft tissues in mouth.

Shifting such responsibility to users is leading to a sub-optimal experience as users (i) either insufficiently cover their teeth with whitening gel to avoid interaction with tissue, or worse (ii) apply whitening gel on their gums which undesirably leads to potential tissue damage.

Accordingly, an appliance which is configured for use with a whitening formulation effective for tooth whitening, and which provides reliable protection for soft tissues, i.e. the gums, is desired. An improved method and apparatus for overcoming the problems in the art is also desired.

In accordance with one aspect, an apparatus for automatically dispensing a teeth whitening substance onto one or more teeth of a user comprises a fluid reservoir, a nozzle having an output port, a fluid dispenser, a sensor and a controller. The fluid reservoir is configured to receive the teeth whitening substance. The fluid dispenser is coupled between the fluid reservoir and the nozzle, wherein the fluid dispenser is configured to dispense the teeth whitening substance from the fluid reservoir to the nozzle, wherein the teeth whitening substance is output via the output port. The sensor is positioned for viewing in an advance dispensing direction of the nozzle and configured to sense a target surface that comprises either (i) a tooth surface or (ii) a surface other than the tooth surface in the advance dispensing direction of the nozzle. The controller is operatively coupled between the sensor and the fluid dispenser for (i) controlling a gating of the fluid dispenser to dispense the teeth whitening substance from the fluid reservoir in response to the sensor detecting the tooth surface, and (ii) stopping or disabling the gating of the fluid dispenser to stop or disable a dispensing of the teeth whitening substance from the fluid reservoir in response to the sensor detecting the surface other than a tooth surface.

In accordance with another aspect, the apparatus further comprises a user guidance feedback module configured to provide at least one user perceptible feedback signal indicative of at least one of the tooth surface and the surface other than the tooth surface in response to the sensor sensing at least one of the tooth surface and the surface other than the tooth surface in the advance dispensing direction of the nozzle. With this embodiment, the controller is further responsive to a user input in response to the perceptible feedback signal for controlling the gating of the fluid dispenser to dispense the teeth whitening substance from the fluid reservoir in response to the sensor detecting the tooth surface, and (ii) stopping or disabling the gating of the fluid dispenser to stop or disable a dispensing of the teeth whitening substance from the fluid reservoir in response to the sensor detecting the surface other than a tooth surface.

In one embodiment, the fluid dispenser can comprise a pump coupled between the fluid reservoir and the nozzle, wherein the pump is configured dispense a targeted quantity of the teeth whitening substance from the fluid reservoir to the nozzle in response to the pump being gated via the controller. In addition, the nozzle can comprise a pump nozzle of the fluid dispenser pump. In another embodiment, the fluid dispenser pump is a manual pump and the controller gates a functionality of the mechanical pump by triggering of a mechanical part blocking activation of the manual pump.

In another embodiment, the sensor is further aligned with the nozzle to capture data relating to a type of surface facing the nozzle. Still further, in one embodiment, the sensor further comprises a surface detection module having a field of view configured to estimate a type of surface in the field of view. According to still another embodiment, the sensor is sensitive to at least one selected from the group consisting of: (I) at least two ultraviolet (UV), visible, near-infrared (NIR) or infrared wavelengths, and wherein the sensor further includes an optical sensor module that comprises at least one selected from the group consisting of (i) an optical fiber, (ii) an image sensor, and (iii) at least one photocell, and (II) an air pressure, and wherein the sensor further includes a pressure sensor coupled with a corresponding air flow source, and a hollow tip air nozzle configured to make contact with (i) the tooth surface and (ii) the surface other than the tooth surface in the advance dispensing direction of the nozzle. According to another embodiment, the sensor is further configured to differentiate between (i) a clean tooth surface in which a presence of plaque is less than a threshold amount and (ii) a tooth surface presenting plaque greater than the threshold amount, wherein the controller is further configured to not gate the fluid dispenser in response to the sensor detecting a tooth surface presenting plaque.

According to one embodiment, the user guidance feedback module is further configured to provide, for a current tooth surface in a whitening routine, the at least one user perceptible feedback signal indicative of at least one of (i) the current tooth surface has a presence of plaque greater than a threshold amount and is needing to be cleaned before proceeding with the whitening routine, (ii) an extra amount of teeth whitening substance is being dispensed to compensate for the presence of plaque greater than the threshold amount, or (iii) a user selectable option to (iii)(a) pause the whitening routine to allow cleaning of plaque from the current tooth surface or (iii)(b) dispense the extra amount of teeth whitening substance in the presence of plaque. In addition, the surface other than the tooth surface can comprise at least (i) a tissue surface or (ii) at least a portion of a tooth surface already covered with teeth whitening substance.

In yet another embodiment, the controller is further configured to log, via a memory, an amount of teeth whitening substance dispensed by the fluid dispenser and to track a total amount of teeth whitening substance used during a whitening routine. In addition, the gating of the fluid dispenser (20) to dispense the teeth whitening substance comprises gating a limited controlled quantity of the teeth whitening substance. Furthermore, the user perceptible feedback includes at least one of an audio signal, a visual signal, a haptic signal, and feedback via a digital media signal output for reception on an external media device.

In other embodiments, the sensor is configured to capture samples of sensor data at a capture rate for at least ensuring a user's motion can be characterized. The fluid reservoir is further configured to store a quantity of teeth whitening substance that is sufficient for treating a complete set of teeth in one teeth whitening routine. In addition, the teeth whitening substance can comprise a liquid, a gel, or a combination of a liquid and gel. Furthermore, the nozzle can comprise a single tip nozzle having only one opening for outputting the teeth whitening substance.

According to another embodiment, a method for automatically dispensing, via a whitening apparatus, a teeth whitening substance onto one or more teeth of a user comprises: receiving, via a fluid reservoir, the teeth whitening substance; coupling a fluid dispenser between the fluid reservoir and a nozzle having an output port, wherein the fluid dispenser is configured to dispense the teeth whitening substance from the fluid reservoir to the nozzle, and wherein the teeth whitening substance is output via the output port; positioning a sensor for viewing in an advance dispensing direction of the nozzle, wherein the sensor is configured to sense a target surface that comprises either (i) a tooth surface or (ii) a surface other than the tooth surface in the advance dispensing direction of the nozzle; and controlling, via a controller operatively coupled between the sensor and the fluid dispenser, (i) a gating of the fluid dispenser to dispense the teeth whitening substance from the fluid reservoir in response to the sensor detecting the tooth surface, and (ii) stopping or disabling the gating of the fluid dispenser to stop or disable a dispensing of the teeth whitening substance from the fluid reservoir in response to the sensor detecting the surface other than a tooth surface.

In another embodiment, the method further comprises providing at least one user perceptible feedback signal, via a user guidance feedback module, indicative of at least one of the tooth surface and the surface other than the tooth surface in response to the sensor sensing at least one of the tooth surface and the surface other than the tooth surface in the advance dispensing direction of the nozzle.

In accordance with another aspect, a method and system apparatus automatically dispenses whitening chemicals only on tooth surfaces by (i) automatically detecting on what type of surface a whitening dispenser is being applied, and (ii) gating the whitening chemical dispenser. An advantage and main benefit delivered by the method disclosed herein is that it allows a user to optimally and safely experience an in-home whitening process by ensuring that whitening chemical is only applied where it truly matters.

Still further advantages and benefits will become apparent to those of ordinary skill in the art upon reading and understanding the following detailed description.

The embodiments of the present disclosure may take form in various components and arrangements of components, and in various steps and arrangements of steps. Accordingly, the drawings are for purposes of illustrating the various embodiments and are not to be construed as limiting the embodiments. In the drawing figures, like reference numerals refer to like elements.

FIG. 4 (4A, 4B, 4C) is a collection of views of a portion of the sensor according to one embodiment of the present disclosure.

The embodiments of the present disclosure and the various features and advantageous details thereof are explained more fully with reference to the non-limiting examples that are described and/or illustrated in the drawings and detailed in the following description. It should be noted that the features illustrated in the drawings are not necessarily drawn to scale, and features of one embodiment may be employed with other embodiments as the skilled artisan would recognize, even if not explicitly stated herein. Descriptions of well-known components and processing techniques may be omitted so as to not unnecessarily obscure the embodiments of the present disclosure. The examples used herein are intended merely to facilitate an understanding of ways in which the embodiments of the present may be practiced and to further enable those of skill in the art to practice the same. Accordingly, the examples herein should not be construed as limiting the scope of the embodiments of the present disclosure, which is defined solely by the appended claims and applicable law.

It is understood that the embodiments of the present disclosure are not limited to the particular methodology, protocols, devices, apparatus, materials, applications, etc., described herein, as these may vary. It is also to be understood that the terminology used herein is used for the purpose of describing particular embodiments only, and is not intended to be limiting in scope of the embodiments as claimed. It must be noted that as used herein and in the appended claims, the singular forms "a," "an," and "the" include plural reference unless the context clearly dictates otherwise.

Unless defined otherwise, all technical and scientific terms used herein have the same meanings as commonly understood by one of ordinary skill in the art to which the embodiments of the present disclosure belong. Preferred methods, devices, and materials are described, although any methods and materials similar or equivalent to those described herein can be used in the practice or testing of the embodiments.

Figure 1:
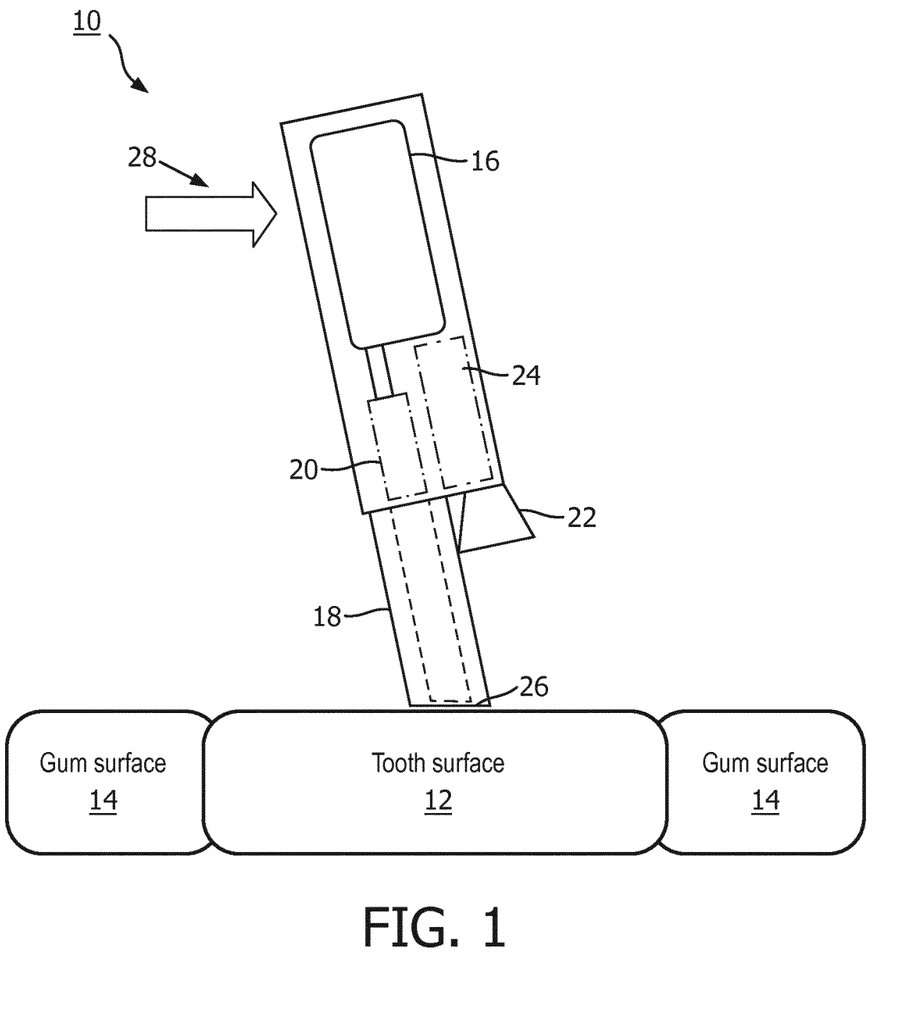
FIG. 1 is a schematic diagram view of the whitening smart pen apparatus for automatically dispensing a teeth whitening substance onto teeth of a user, which provides a level of protection of soft tissues during dispensing of the teeth whitening substance for the teeth whitening process, according to an embodiment of the present disclosure.

With reference now to FIG. 1, there is shown a schematic diagram view of a whitening smart pen apparatus 10 for automatically dispensing a teeth whitening substance onto a tooth 12 of a user, according to an embodiment of the present disclosure. The whitening smart pen apparatus 10 is configured to provide a level of protection for soft tissues (gums, cheeks, tongue) 14 during dispensing of the teeth whitening substance for the teeth whitening process. The whitening smart pen apparatus 10 comprises at least a fluid reservoir 16, a nozzle 18, a fluid dispenser 20, a sensor 22, and a controller 24. The fluid reservoir 16 is configured to receive a teeth whitening substance. The fluid reservoir 16 can be further configured to store a quantity of teeth whitening substance that is sufficient for treating a complete set of teeth in one teeth whitening routine. The teeth whitening substance preferably comprises a liquid, a gel, a paste, or a combination thereof. In other embodiments, the volume of the reservoir can depend on both the mass of gel for each treatment and the number of treatments. For example, a treatment may be uni-dose, or the treatment may have all gel stored in one single primary package. Further examples include a package size (i.e., reservoir volume) that may include take-home whitening products in one package and varnish in another container. Still further, the embodiments herein are not limited to be used with any special chemical formulations, so the mass of whitening gel applied to the teeth will be different from product to product. Usually, if the viscosity is lower, a lesser amount of gel will be used per application (e.g., one treatment). Furthermore, the amount of gel can be, for example, in the range from 0.1 g to 2.0 grams for each treatment.

The nozzle 18 (or pen tip) can include an output port 26 of various nozzle designs. For example, the nozzle 18 can comprise a single tip nozzle having only one output port 26, for dispensing the teeth whitening substance, wherein the opening size varies depending on the viscosity of the fluid being dispensed. In another design, the nozzle 18 comprises a pump nozzle of a fluid dispenser pump, as will be discussed further herein below. In a further design, the pump nozzle can include an actuator (not shown) configured to cover and uncover the output port 26 of the nozzle 18. With respect to the latter design, the actuator (not shown) comprises at least one selected from the group consisting of a piezoelectric actuator, a dc motor with gate mechanism, or a shape memory alloy. Generally, the nozzle 18 is coupled to the fluid reservoir 16 and has an output port 26 configured to output the teeth whitening substance from the fluid reservoir.

The fluid dispenser 20 is coupled between the fluid reservoir 16 and the nozzle 18. The fluid dispenser 20 is configured to dispense the teeth whitening substance from the fluid reservoir to the nozzle 18, wherein the teeth whitening substance is output via the output port 26. In one embodiment, the fluid dispenser 20 comprises a pump coupled between the fluid reservoir 16 and the nozzle 18. The pump is configured dispense a targeted quantity of the teeth whitening substance from the fluid reservoir to the nozzle in response to the pump being gated via the controller 24. In one embodiment, the controller 24 can be configured to serve as a gate to functionality of the fluid dispenser pump 20, for example, with an electrical bypass circuit (not shown). In another embodiment, the fluid dispenser pump 20 comprises a manual pump and the controller 24 gates a functionality of the mechanical pump by triggering of a mechanical part (not shown) blocking activation of the manual pump. For example, the mechanical part may include a twist screw bolt or a pressure piston.

With reference still to FIG. 1, the sensor 22 is positioned at any suitable location of the apparatus 10 such that it can sense a target surface area where liquid or gel would be dispensed from the nozzle 18 if dispensed. In one embodiment, sensor 22 is positioned to sense in an advance dispensing direction in front of the nozzle 18, i.e., in a forward traversing direction of the nozzle 18, as indicated by arrow 28. As used herein, the advanced dispensing direction refers to a direction that is pointed to by the nozzle, to which whitening substance would be dispensed, if dispensed. In addition, the sensor 22 is configured to sense a target surface that comprises either (i) a tooth surface 12 or (ii) a tissue surface 14 other than the tooth surface in the advance dispensing direction of the nozzle. For instance, the surface 14 other than the tooth surface can comprise a gum tissue surface. In addition, the sensor 22 is preferably (i) positioned in the advance dispensing direction in front of the nozzle and (ii) aligned with the nozzle 18 to capture data relating to a type of surface the nozzle is approaching.

The controller 24 is operatively coupled between the sensor 22 and the fluid dispenser 20 for (i) controlling a gating of the fluid dispenser 20 to dispense a limited controlled quantity of the teeth whitening substance from the fluid reservoir 16 in response to the sensor 22 detecting the tooth surface 12. The controller 24 is further configured for (ii) stopping or disabling the gating of the fluid dispenser 20 to stop or disable a dispensing of the teeth whitening substance from the fluid reservoir 16 in response to the sensor 22 detecting a surface 14 other than a tooth surface. Further detail of the controller is provided herein below in the description with reference to FIG. 3.

As will become apparent herein, the embodiments of the present disclosure advantageously provide that a whitening substance is only delivered as necessary, i.e., the appropriate amount on the tooth surfaces with guidance feedback to the user and the well-controlled dispensing of whitening substance. The embodiments further advantageously provide a guided and well controlled dispensing device. In one embodiment, the device and method use only one gated nozzle for accurate whitening substance dispensing. Prior known methods can be adversely affected because they detect the tooth surface after applying a whitening substance while the embodiments of the present disclosure do not have this issue because the embodiments of the present disclosure detect the surface before applying any whitening substance. The embodiments of the present disclosure advantageously provide a smart whitening pen that knows not only to dispense whitening chemistry when over a tooth, but also knows to stop dispensing (i.e., not dispense) when the dispenser tip is over, or about to go over, soft tissue. For example, the device and method advantageously use the sensor 22 to scan the target surface and the electronic control 24 to vary the fluid dispensed to the target surface, as will be further discussed herein. Furthermore, some whitening substances could utilize an optical based sensor determination method because of color of the whitening substance being dispensed.

Figure 2:
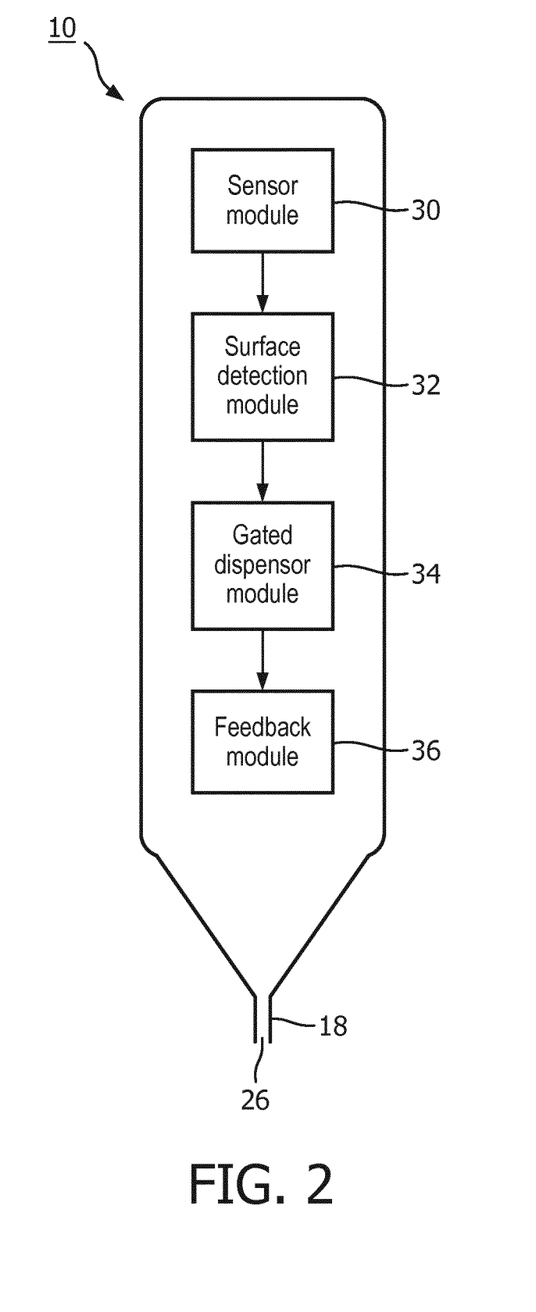
FIG. 2 is a block diagram view of components of the whitening smart pen apparatus for automatically dispensing a teeth whitening substance onto teeth of a user according to an embodiment of the present disclosure.

Turning now to FIG. 2, there is shown a block diagram view of components of the whitening smart pen apparatus 10 for automatically dispensing a teeth whitening substance according to an embodiment of the present disclosure. The whitening smart pen apparatus 10 includes a sensor module 30, a surface detection module 32, a gated dispenser module 34, and a user feedback module 36. The surface detection module 32 is configured to estimate the surface being examined by one or more sensors 22 (FIG. 1) of the sensor module 30. The gated dispenser module 34 is configured to control an amount of whitening chemical being dispensed.

In a preferred embodiment, the sensor module 30 is embedded in the whitening smart pen apparatus 10 and aligned with the chemical dispense nozzle 18 to capture data of the surface facing the output port 26 of the dispenser nozzle. In one embodiment, the sensor module 30 comprises, but is not limited to, an optical sensor coupled to a corresponding light source and configured to allow for a characterization of the wavelength being reflected by a surface facing the dispense nozzle output port 26. Such an optical sensor module can comprise any one or more of the following (or a combination thereof): (i) an optical fiber being sensitive to at least one of UV, Visible, NIR or Infrared wavelengths, (ii) an image sensor being sensitive to at least one of UV, Visible, NIR or Infrared wavelengths, and (iii) at least one photocell being sensitive to at least one of UV, Visible, NIR or Infrared wavelengths.

In another embodiment, the sensor module 30 includes at least one sensor 22 (FIG. 1) that is sensitive to at least one selected from the group consisting of: (I) at least one of ultraviolet (UV), visible, near-infrared (NIR) or infrared wavelengths, and wherein the sensor further includes an optical sensor module that comprises (i) an optical fiber, (ii) an image sensor, and at least one photocell, each having a field of view that includes (i) the tooth surface 12 or (ii) the surface 14 other than the tooth surface in the advance dispensing direction 28 (FIG. 1) of the nozzle 18. As disclosed herein, the surface 14 other than the tooth surface can comprise at least (i) a gum, cheek, tongue or mouth tissue surface or (ii) at least a portion of a tooth surface that is already covered with teeth whitening substance.

Figure 4A:
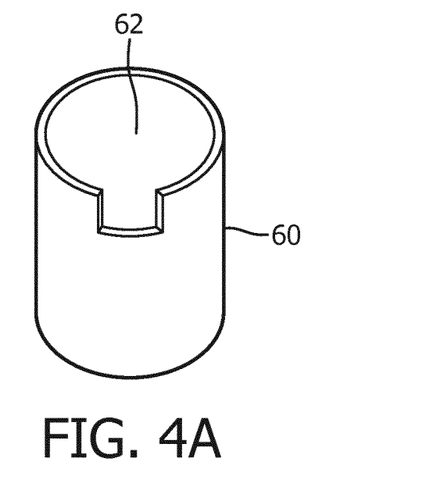
Figure 4B:
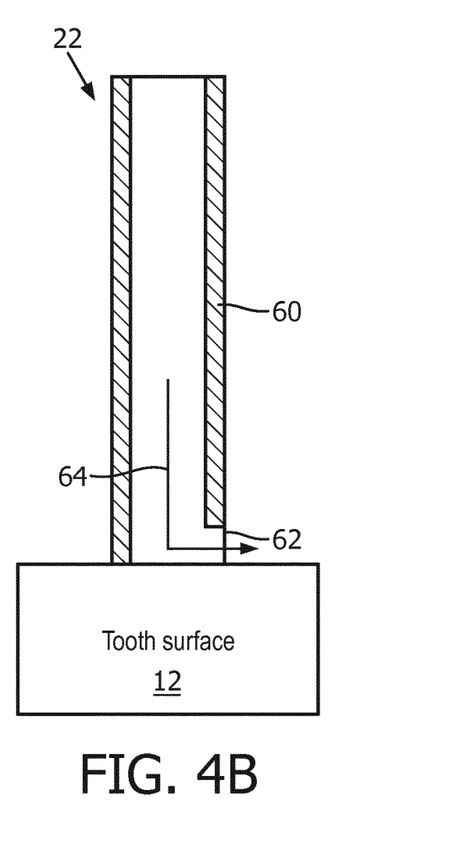
Figure 4C:
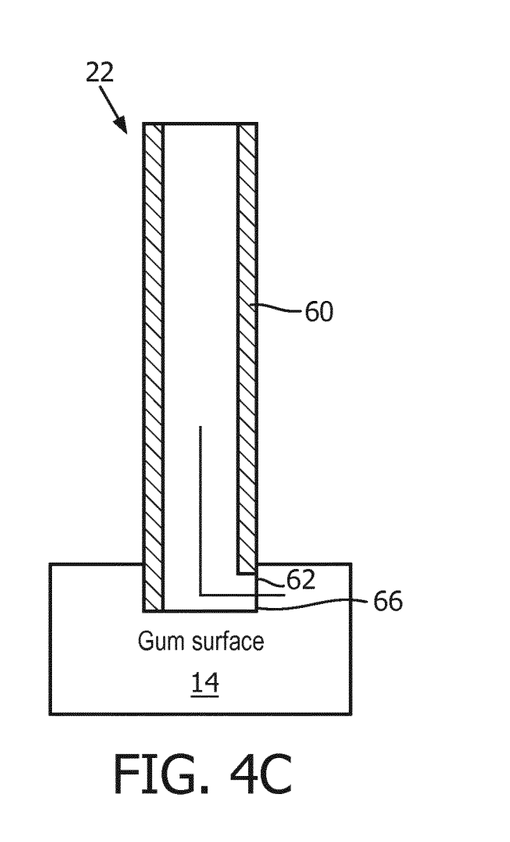

In yet another embodiment, the sensor 22 of the sensor module 30 can include a pressure sensor that is sensitive to air pressure which is coupled with a corresponding air flow source and a fine hollow tip air nozzle 60 (FIG. 4). A distal end of the hollow tip air nozzle 60 features at least one cut-out 62 or ridge (FIG. 4A) in a rim of the tip which function as pressure relief geometries in response to the distal end of the hollow tip air nozzle being pressed against a hard surface, such as a tooth surface 12. The at least one cut-out 62 or ridge provides at least one air path 64 for air flow to escape, even if the hollow tip air nozzle is pressed flush against a tooth surface 12 (FIG. 4B). However, the at least one cut-out 62 or ridge in the rim of the tip will fill with soft tissue in response to the distal end of the hollow tip air nozzle being pressed against a soft tissue surface, such as a gum surface 14. The gum surface 14 comprises soft tissue which is deformable enough to clog the at least one cut-out 62 or ridge in the rim of the tip (FIG. 4C). The clogging creates a difference in pressure and flow rate, which can be detected. In other words, the blockage 66 of the nozzle tip by soft matter (e.g., tissue or whitening substance) will cause a pressure increase and a flow rate decrease. In addition, an inner diameter of the air nozzle tip 60 can range from sub-millimeter to a few millimeters. In this embodiment, air from the air flow source is output via the hollow tip air nozzle 60 and configured to make contact with (i) the tooth surface 12 or (ii) the surface 14 other than the tooth surface in the advance dispensing direction 28 (FIG. 1) of the nozzle 18. As disclosed herein, the surface other than the tooth surface can comprise at least (i) a gum or mouth tissue surface or (ii) at least a portion of a tooth surface that is already covered with teeth whitening substance.

In a further embodiment, the sensor 22 of the sensor module 30 is selected based on its ability to capture samples of sensor data at a capture rate for at least ensuring a user's motion can be characterized. In one embodiment, the capture rate is greater than 20 Hz, and more preferably, greater than at least 10 Hz.

The whitening smart pen apparatus 10 further comprises a surface detection module 32 configured to estimate a type of surface in the field of view of the sensor module 30. In one embodiment, the surface detection module 32 is further configured to exploit at least one difference in two types of surfaces via at least one of (i) template matching and (ii) extraction of reflectance ratios. In a preferred embodiment that includes the use of an optical sensor in combination with a light source, the surface detection is obtained by comparing the properties of the light reflected by the surface being observed. Gums 14 and teeth 12 exhibit clearly distinguishable reflectance properties: (i) a tooth 12 exhibits a very smooth reflectance spectra, (ii) whereas gums 14 exhibit varying reflectance spectra due to the light absorption of chromophores present in the gums tissue (i.e., mostly composed of haemoglobin).

The surface detection module 32 exploits these differences in reflectance properties by using any of the following methods or a combination of the same, which include template matching techniques and extraction of reflectance ratios. With respect to template matching techniques, a distance metric is used to determine which of the two surfaces is being examined. In addition, a distance metric can be defined by a norm of distance between measurement and template. Furthermore, a correlation value is determined between measurement and template. With respect to an extraction of reflectance ratios at a targeted wavelength or group of wavelengths, the technique makes use of data, such as that presented in the light reflectance spectra for gums 14 and teeth 12. For example, a typical ratio of reflectance at 660 nm and 550 nm would provide values of 2.38 and 1.21 for gums and teeth, respectively. In addition, a ratio of reflectance between a "blue" (400 nm-480 nm) and a "green" (480 nm-550 nm) band would provide values of 5.96 and 1.44 for gums and teeth, respectively. It can be appreciated that this is merely an example; other wavelengths and ranges may also be possible. In another embodiment, the detection may be manually/remotely inputted, e.g., wired or wireless communications, into the white smart pen apparatus by an expert, e.g., home whitening with professional assistance to provide users with reassurance and/or confirmation, as will be further understood with respect to the discussion of the embodiment of FIG. 3 herein below.

With reference again to FIGS. 1 and 2, the surface detection module 32 of the whitening smart pen apparatus 10 may further be configured to differentiate between (i) a clean tooth surface and (ii) a tooth surface presenting biofilm (e.g. plaque) greater than the threshold amount, wherein the controller 24 is further configured to not gate the fluid dispenser 20 in response to the sensor 22 detecting a tooth surface 12 presenting plaque.

Further in connection with the fluid dispenser 20 (also referred to herein as the gated dispenser module 34), the controller 24 is configured to log, via a memory (FIG. 3), an amount of teeth whitening substance dispensed by the fluid dispenser 20 and to track a total amount of teeth whitening substance used during a whitening routine. In addition, the controller 24 can be configured to control the fluid dispenser 20 or gated dispenser module 34 for gating of the fluid dispenser 20 to dispense a limited controlled quantity of the teeth whitening substance. In one embodiment, the limited controlled quantity can comprise any suitable volume determined according to the requirements for a given teeth whitening application or routine.

In a preferred embodiment, the fluid dispenser 20 or gated dispenser module 34 comprises (i) a pump for dispensing a targeted amount of chemical when triggered and (ii) a pump control mechanism for controlling the pump based on the output of the surface detection mechanism. The pump control mechanism may comprise a pump nozzle with an actuator to cover or uncover the nozzle based on the output of the surface detection module 32, such as, a piezoelectric actuator, a DC motor with gate mechanism, and/or a shape memory alloy. The pump control mechanism may further comprise an electronic circuit enabling or disabling the pump circuit based on the output of the surface detection module 32. For example, the electronic circuit may include an electrical bypass of the pump functionality in an electric pump embodiment, and a trigger of a mechanical part blocking the activation of a pump in a manual pump embodiment (e.g., a twist screw bolt, a pressure piston, etc.). In yet another embodiment, the fluid dispenser 20 or gated dispenser module 34 logs the amount of a chemical dispense event in a back-end system (e.g., an internal memory, a digital media in case of a network connected whitening smart pen device) to allow user to track the amount of the chemical used during a whitening routine.

With reference still to FIG. 2, the feedback module 36 is configured to provide at least one user perceptible feedback signal indicative of at least one of (i) the tooth surface 12 and (ii) the surface 14 other than the tooth surface in response to the sensor module 30 and surface detection module 32 sensing and detecting, respectively, at least one of the tooth surface 12 and the surface 14 other than the tooth surface in the advance dispensing direction 28 of the nozzle 18. Feedback provided to a user by the feedback module 36 can include one or more of an audio signal, a visual signal, or a haptic signal. In another embodiment, where remote or network connectivity is available, the feedback can further be provided on a digital media or via a digital media signal.

In one embodiment, the user guidance feedback module 36 is further configured to provide, for a current tooth surface pointed to via the whitening smart pen 10 in a whitening routine, the at least one user perceptible feedback signal can further be indicative of at least one of (i) the current tooth surface has a presence of biofilm greater than a threshold amount and is needing to be cleaned before proceeding with the whitening routine, (ii) an extra amount of teeth whitening substance is being dispensed to compensate for the presence of plaque greater than the threshold amount, or (iii) a user selectable option to (iii)(a) pause the whitening routine to allow cleaning of plaque from the current tooth surface or (iii)(b) dispense the extra amount of teeth whitening substance in the presence of plaque.

In the embodiment in which the sensor 22 of the sensor module 30 includes a pressure sensor coupled with a corresponding air flow source as discussed previously herein, the air flow pressure enables the differentiation between clean teeth and teeth presenting plaque. As clean teeth are desired to ensure optimal whitening results, a corresponding input on the presence of plaque can be added in the surface detection module 32. The surface detection module 32 can communicate the presence of plaque to the control module 24 and/or the feedback module 36. The feedback module 36 can then provide feedback to a user that the whitening chemical will not be applied since the particular tooth currently being pointed to via the whitening smart pen 10 requires cleaning first. Alternatively, the feedback module 36 could provide feedback to the user indicative that an extra amount of whitening chemical is being dispensed, via the controller 24 controlling the gated dispenser module 34, to compensate for the presence of bio film and thereby obtain results similar as those obtained on clean teeth. In the later example, the gated dispenser module 34 is gated to dispense the extra amount of whitening chemical to compensate for the presence of biofilm.

Figure 3:
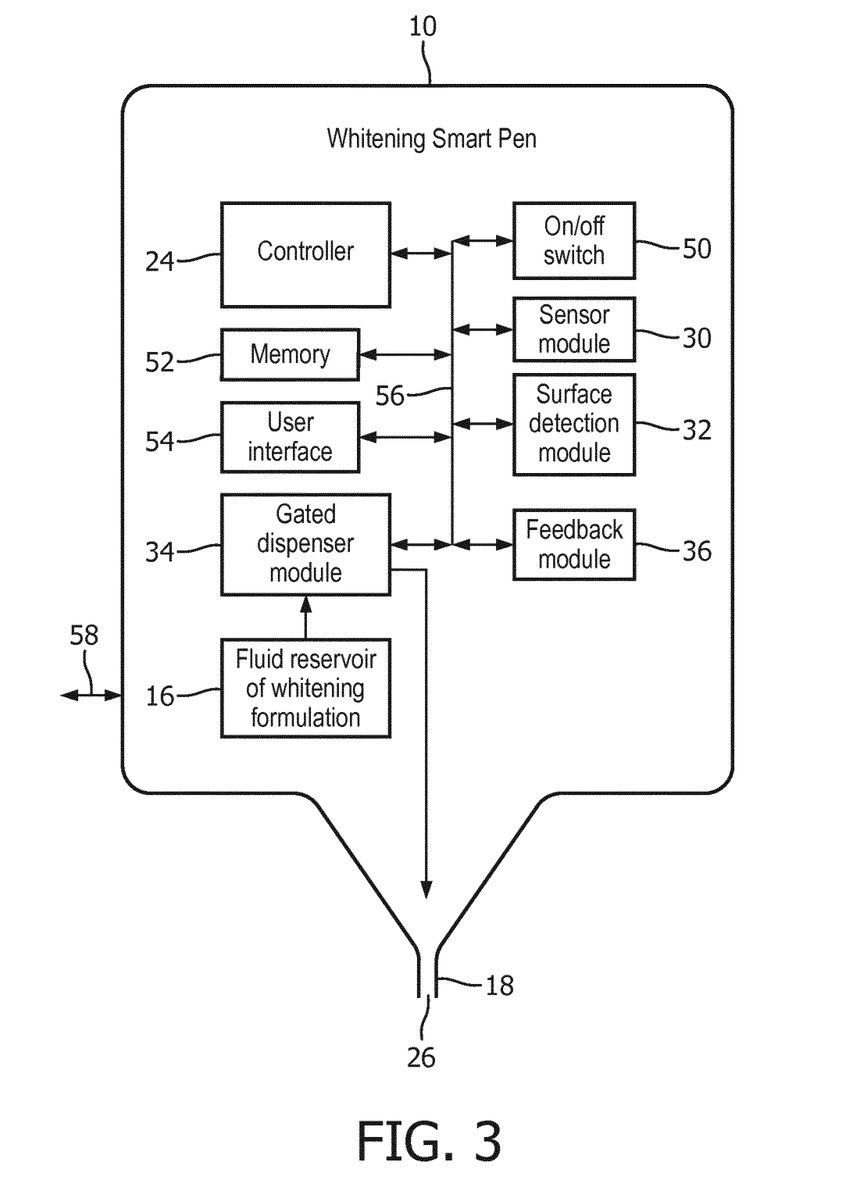
FIG. 3 is a further block diagram view of components of the whitening smart pen apparatus for automatically dispensing a teeth whitening substance onto teeth of a user according to an embodiment of the present disclosure.

With reference now to FIG. 3, there is shown a further block diagram view of components of the whitening smart pen apparatus 10 for automatically dispensing a teeth whitening substance onto teeth of a user according to another embodiment of the present disclosure. The embodiment of FIG. 3 is similar to the embodiments previously described herein with the following differences. As illustrated, the whitening smart pen 10 comprises at least a fluid reservoir 16, a nozzle 18, a gated dispenser module 34, a sensor module 30, a surface detection module 32, a feedback module 36, and a controller 24. The whitening smart pen 10 can further comprise an on/off switch 50, a memory 52, and a user interface 54. The on/off switch 50 and/or the user interface 54 are configured for at least initiating the method according to one or more of the various embodiments discussed herein. The user interface 54 comprises any suitable user interface operatively coupled to at least the controller 24, via signal lines 56, for use in connection with and/or during a teeth whitening routine, as discussed further herein. For example, user interface 54 can comprise a graphical user interface operatively coupled to at least the controller 24, via signal lines 56, for use in connection with a given teeth whitening device implementation and/or application, as discussed further herein. Still further, the whitening smart pen 10 can comprise a wired and/or wireless connection, for example, as indicated via reference numeral 58, wherein the controller 24 is further configured for implementing wired or wireless communications, via the connection 58, with a remote device or network (not shown).

User interface 54 is configured to provide an interface between system 10 and a user through which the user may provide information to and receive information from system. The user interface 54 enables one or more of data, results, and/or instructions and any other communicable items, collectively referred to as "information," to be communicated between the user and system 10. An example of information that may be conveyed to user is a report detailing trends in the user's whitening routines throughout a period during which the user is receiving the teeth whitening treatment. Another example of information that may be conveyed to the user is an alarm or unsafe condition (e.g., the nozzle pointing to gum or surfaces other than teeth) detected by system 10. Examples of interface devices suitable for inclusion in user interface 54 include a keypad, buttons, switches, a keyboard, knobs, levers, a display screen, a touch screen, speakers, a microphone, an indicator light, an audible alarm, and a printer. Information may be provided to the user by user interface 54 in the form of auditory signals, visual signals, tactile signals, and/or other sensory signals. In one embodiment, the user interface 54 may be integrated with a removable storage interface provided by a database or storage (not shown). In such an example, information is loaded into system 10 from removable storage (e.g., a smart card, a flash drive, a removable disk, etc.) that enables the user to customize the implementation of system. Other techniques for communicating information with system 10 are contemplated as user interface 54.

With reference still to FIG. 3, controller 24 is shown operatively coupled with on/off switch 50, memory 52 and user interface 54. Controller 24 further interacts with one or more modules that include at least the sensor module 30, the surface detection module 32, the gated dispenser module 34, and the feedback module 36, as discussed further herein. Furthermore, controller 24 can be configured for a wired or wireless communications connection with a remote device or network, for example, as indicated via reference numeral 58.

In one embodiment, controller 24 comprises one or more of a microprocessor, microcontroller, field programmable gate array (FPGA), integrated circuit, discrete analog or digital circuit components, hardware, software, firmware, or any combination thereof, for performing various functions as discussed herein, further according to the requirements of a given ventilator system apparatus implementation and/or application. Controller 24 can further comprise one or more of the various modules as discussed herein. Additional details regarding the controller 24 are provided herein with reference to the Figures. In addition, the modules 30-36 can comprise one or more of an integrated circuit, discrete analog or digital circuit components, hardware, software, firmware, or any combination thereof, for performing various functions as discussed herein, further according to the requirements of a given teeth whitening apparatus implementation and/or application. Furthermore, one or more of the modules 30-36 can further comprise various combinations of one or more of the various modules.

According to another embodiment, a method is provided for automatically dispensing, via a whitening smart pen apparatus 10, a teeth whitening substance onto one or more teeth of a user. The method comprises: receiving, via a fluid reservoir 16, the teeth whitening substance; coupling a fluid dispenser 20 between the fluid reservoir 16 and a nozzle 18 having an output port 26, wherein the fluid dispenser 20 is configured to dispense the teeth whitening substance from the fluid reservoir to the nozzle; and wherein the teeth whitening substance is output via the output port 26; positioning a sensor 22 in an advance dispensing direction 28 in front of the nozzle 18, wherein the sensor 22 is configured to sense a target surface that comprises either (i) a tooth surface 12 or (ii) a surface 14 other than the tooth surface in the advance dispensing direction of the nozzle; and controlling, via a controller 24 operatively coupled between the sensor 22 and the fluid dispenser 20, (i) a gating of the fluid dispenser 20 to dispense a limited controlled quantity of the teeth whitening substance from the fluid reservoir 16 in response to the sensor 22 detecting the tooth surface 12, and (ii) stopping or disabling the gating of the fluid dispenser 20 to stop or disable a dispensing of the teeth whitening substance from the fluid reservoir 16 in response to the sensor 22 detecting the surface 14 other than a tooth surface. The method further comprises providing at least one user perceptible feedback signal, via a user guidance feedback module 36, indicative of at least one of the tooth surface 12 and the surface 14 other than the tooth surface in response to the sensor 22 sensing at least one of the tooth surface and the surface other than the tooth surface in the advance dispensing direction 28 of the nozzle 18.

Although only a few exemplary embodiments have been described in detail above, those skilled in the art will readily appreciate that many modifications are possible in the exemplary embodiments without materially departing from the novel teachings and advantages of the embodiments of the present disclosure. For example, the embodiments of the present disclosure can be advantageously used in a gel/fluid dispenser part of an oral healthcare device or in a dedicated device that is part of an oral care routine. For example, the embodiments may include (1) a pen-like dispenser for a person to use to apply a whitening chemistry or (2) a mouthpiece with dispenser holes, that incorporates a sensor module that can determine if the dispenser tip/hole is in contact with teeth, or soft tissue, and if the latter, it will not dispense the whitening chemistry. In another arrangement, instead of having a gate that turns on/off the dispenser, the system can provide an audio or visual feedback to the user if the dispenser is in contact with soft tissue. Still further, a combination of turning the dispenser off and providing an alarm to the user can be provided. The method and system embodiments of the present disclosure can also be applied to one or more of the following examples. In one example, a mouthpiece can be used in the context of whitening, where the method disclosed herein is carried out simultaneously on an array of sensor/gated dispenser modules. In another example, a system is composed of two elements in which the sensor(s) is (are) located in a device that is only used to provide data to the surface detection module (e.g., a camera transmitting data to an App) and where the gated dispenser module is located in a separate device. In a further example, an application is targeted at the detection of different surfaces, where the surface detection module is tuned towards different wavelengths, e.g., for dispensing only on a desired surface detected via the tuned wavelength. Accordingly, all such modifications are intended to be included within the scope of the embodiments of the present disclosure as defined in the following claims. In the claims, means-plus-function clauses are intended to cover the structures described herein as performing the recited function and not only structural equivalents, but also equivalent structures.

In addition, any reference signs placed in parentheses in one or more claims shall not be construed as limiting the claims. The word "comprising" and "comprises," and the like, does not exclude the presence of elements or steps other than those listed in any claim or the specification as a whole. The singular reference of an element does not exclude the plural references of such elements and vice-versa. One or more of the embodiments may be implemented by means of hardware comprising several distinct elements, and/or by means of a suitably programmed computer. In a device claim enumerating several means, several of these means may be embodied by one and the same item of hardware. The mere fact that certain measures are recited in mutually different dependent claims does not indicate that a combination of these measures cannot be used to an advantage.

The invention claimed is:

1. An apparatus for automatically dispensing a teeth whitening substance, the apparatus comprising:
   a fluid reservoir configured to receive the teeth whitening substance;
   a nozzle having an output port;
   a fluid dispenser coupled between the fluid reservoir and the nozzle, wherein the fluid dispenser is configured to dispense the teeth whitening substance from the fluid reservoir to the nozzle, wherein the teeth whitening substance is output via the output port;
   a sensor positioned for viewing in an advance dispensing direction of the nozzle, wherein the sensor is configured to sense a target surface that comprises either (i) a tooth surface or (ii) a surface other than the tooth surface in the advance dispensing direction of the nozzle; and
   a controller operatively coupled between the sensor and the fluid dispenser for controlling a gating of the fluid dispenser to dispense the teeth whitening substance from the fluid reservoir in response to the sensor detecting the tooth surface, and while the fluid dispenser dispenses the teeth whitening substance and in response to the sensor detecting the surface other than a tooth surface stopping or disabling the gating of the fluid dispenser to stop or disable a dispensing of the teeth whitening substance from the fluid reservoir.

2. The apparatus of claim 1, further comprising:
   a user guidance feedback module configured to provide at least one user perceptible feedback signal indicative of at least one of the tooth surface and the surface other than the tooth surface in response to the sensor sensing at least one of the tooth surface and the surface other than the tooth surface in the advance dispensing direction of the nozzle, and wherein the controller is further responsive to a user input in response to the perceptible feedback signal for controlling the gating of the fluid dispenser to dispense the teeth whitening substance from the fluid reservoir in response to the sensor detecting the tooth surface, and (ii) stopping or disabling the gating of the fluid dispenser to stop or disable a dispensing of the teeth whitening substance from the fluid reservoir in response to the sensor detecting the surface other than a tooth surface.

3. The apparatus of claim 1, wherein the fluid dispenser comprises a pump coupled between the fluid reservoir and the nozzle, wherein the pump is configured to dispense a targeted quantity of the teeth whitening substance from the fluid reservoir to the nozzle in response to the pump being gated via the controller.

4. The apparatus of claim 1, wherein the sensor further comprises a surface detection module having a field of view configured to estimate a type of surface in the field of view.

5. The apparatus of claim 1, wherein the sensor is sensitive to at least one selected from the group consisting of:
(I) at least two ultraviolet (UV), visible, near-infrared (NIR) or infrared wavelengths, and wherein the sensor further includes an optical sensor module that comprises at least one selected from the group consisting of (i) an optical fiber, (ii) an image sensor, and (iii) at least one photocell, and
(II) an air pressure, and wherein the sensor further includes a pressure sensor coupled with a corresponding air flow source, and a hollow tip air nozzle configured to make contact with (i) the tooth surface and (ii) the surface other than the tooth surface in the advance dispensing direction of the nozzle.

6. The apparatus of claim 1, wherein the sensor is further configured to differentiate between (i) a clean tooth surface in which a presence of plaque is less than a threshold amount and (ii) a tooth surface presenting plaque greater than the threshold amount, wherein the controller is further configured to stop or disable the dispensing of the whitening substance from the fluid dispenser in response to the sensor detecting the tooth surface presenting plaque greater than the threshold amount.

7. The apparatus of claim 2, wherein the user guidance feedback module is further configured to provide, for a current tooth surface in a whitening routine, the at least one user perceptible feedback signal indicative of at least one of (i) the current tooth surface has a presence of plaque greater than a threshold amount and is needing to be cleaned before proceeding with the whitening routine, (ii) an extra amount of teeth whitening substance is being dispensed to compensate for the presence of plaque greater than the threshold amount, or (iii) a user selectable option to (iii)(a) pause the whitening routine to allow cleaning of plaque from the current tooth surface or (iii)(b) dispense the extra amount of teeth whitening substance in the presence of plaque.

8. The apparatus of claim 1, wherein the surface other than the tooth surface comprises at least (i) a tissue surface or (ii) at least a portion of a tooth surface already covered with teeth whitening substance.

9. The apparatus of claim 1, wherein the gating of the fluid dispenser to dispense the teeth whitening substance comprises gating a limited controlled quantity of the teeth whitening substance.

10. The apparatus of claim 2, wherein the user perceptible feedback includes at least one of an audio signal, a visual signal, a haptic signal, and feedback via a digital media signal output for reception on an external media device.

11. The apparatus of claim 1, wherein the fluid reservoir is further configured to store a quantity of teeth whitening substance that is sufficient for treating a complete set of teeth in one teeth whitening routine.

12. The apparatus of claim 1, wherein the teeth whitening substance comprises a liquid, a gel, or a combination of a liquid and gel.

13. The apparatus of claim 1, further comprising:
a user interface configured to provide an interface between the apparatus and a user through which the user may receive information from the apparatus, wherein the information comprises an indication that the nozzle is pointing to the surface other than a tooth surface.

* * * * *